United States Patent [19]
Snyder et al.

[11] Patent Number: 6,026,689
[45] Date of Patent: Feb. 22, 2000

[54] LOG CUTTING OPTIMIZATION SYSTEM

[75] Inventors: William D. Snyder, Nashville, Ark.; Elmer Christensen, Kent; Stanley L. Floyd, Enumclaw, both of Wash.; Larry H. Jones, DeQueen, Ark.; Calvin K. Kendall, Auburn, Wash.; Billy B. Pearce, DeQueen, Ark.; Everette Shaw, Auburn, Wash.; Michael J. Yancey, Puyallup, Wash.

[73] Assignee: Weyerhaeuser Company, Federal Way, Wash.

[21] Appl. No.: 09/030,608

[22] Filed: Feb. 25, 1998

[51] Int. Cl.[7] .................................................... G01N 9/24
[52] U.S. Cl. ................................ 73/602; 73/597; 73/78; 364/556
[58] Field of Search ............................... 73/78, 587, 594, 73/597, 602; 364/506, 508, 556

[56] References Cited

U.S. PATENT DOCUMENTS

| | | |
|---|---|---|
| 3,196,672 | 7/1965 | Keller . |
| 3,714,820 | 2/1973 | Strickler et al. ............................. 73/89 |
| 4,201,093 | 5/1980 | Logan ........................................ 73/618 |
| 4,418,573 | 12/1983 | Madigosky et al. ...................... 73/574 |
| 4,838,085 | 6/1989 | Pellerin et al. . |
| 4,843,884 | 7/1989 | House et al. .............................. 73/622 |
| 4,852,029 | 7/1989 | Pope et al. ............................... 364/556 |
| 4,856,334 | 8/1989 | Shearer et al. . |
| 4,926,350 | 5/1990 | Bechtel et al. .......................... 364/550 |
| 5,024,091 | 6/1991 | Pellerin et al. .......................... 73/597 |
| 5,060,516 | 10/1991 | Lau et al. ................................. 73/602 |
| 5,097,881 | 3/1992 | Mack . |
| 5,237,870 | 8/1993 | Fry et al. .................................. 73/588 |
| 5,307,679 | 5/1994 | Ross . |
| 5,394,097 | 2/1995 | Bechtel et al. .......................... 324/687 |
| 5,396,799 | 3/1995 | Ross et al. . |
| 5,404,755 | 4/1995 | Olson et al. . |
| 5,503,024 | 4/1996 | Bechtel et al. ............................ 73/852 |
| 5,654,643 | 8/1997 | Bechtel et al. .......................... 324/687 |

OTHER PUBLICATIONS

Ross et al., Stress Wave Nondestructive Evaluation of Logs to Predict Structural Product Quality, Nondestructive Characterization of materials VII, Part 1, 1996.

Anthony, R.W. and Bodig, J. "Nondestructive Evaluation of Timber Structures for Reliable Performance", Engineering Data Management, Inc. Date unknown.

Brochure and Article regarding a Lumber Grading Machine System (translated from Japanese by Ralph McElroy Company, Custom Division) Mar. 1, 1991.

Dunlop, J.I. "Testing of Pole by Acoustic Resonance", *Wood Science and Technology*, 17:31–38 (1983).

Han W. "Log Quality Evaluation by Lengthwise Ultrasonic Transmission" The Norwegian Institute of Wood Technology, Seminar, Oslo, Oct. 25, 1994.

Kaiserlik, J.H. and Pellerin, R.F. "Stress Wave Attenuation as An Indicator of Lumber Strength" *Forest Products Journal*, vol. 27, No. 6, Jun. 1977.

Mokkun Product Specifications, (translated from Japanese by Ralph McElroy Company, Custom Division).

Nakamura, N.; Nanami, N.; Arima, T. "Evaluating the Properties of Standing Trees" Pacific Timber Engineering Conference, Gold Coast Australia, Jul. 11–15, 1994.

(List continued on next page.)

*Primary Examiner*—Elizabeth L. Dougherty
*Attorney, Agent, or Firm*—Christensen, O'Connor, Johnson & Kindness PLLC

[57] ABSTRACT

A system for estimating a velocity of a stress wave induced in a log or tree stem is used to maximize the value of wood products produced. An accelerometer is placed against the log while the log is struck with a pneumatic hammer. By monitoring the signals received at the accelerometer, the velocity of stress wave can be determined. Based on the velocity, an estimate of the modulus of elasticity (MOE) for the wood in the log is made. A price table is selected that relates different sizes of lumber having the determined modulus of elasticity to a current market value. The log is then cut such that the value of the lumber produced is maximized.

10 Claims, 6 Drawing Sheets

OTHER PUBLICATIONS

Nanami, N.; Nakamura, N.; Arima, T.; Okuma, M. "Measuring the Properties of Standing Trees with Stress Waves I. The method of measurement and the propagation path of the waves", *Wood Material Academic Society Magazine* (translated), vol. 38, No. 8, pp. 739–746, 1992.

Nanami, N.; Nakamura; N.; Arima, T.; Okuma, M. "Measuring the Properties of Standing Trees with Stress Waves II. Application of the method to standing trees", *Wood Material Academic Society Magazine* (translated), vol. 38, No. 8, pp. 747–752, 1992.

Nanami, N.; Nakamura, N.; Arima, T.; Okuma, M. "Measuring the Properties of Standing Trees with Stress Waves III. Evaluating the properties of standing trees for some forest stands" *Wood Material Academic Society Magazine* (translated), vol. 39, No. 8, pp. 903–909, 1993.

Ross, R.J.; DeGroot, R.C.; Nelson, W.J. "Technique for Nondestructive Evaluation of Biologically Degraded Wood " *Experimental Techniques*, vol. 18, No. 5, Sep./Oct. 1994.

Ross, R.J.; Fuller, J.J.; Dramm, J.R. "Nondestructuve Evaluation of Green Defect–Prone Red Oak Lumber: A Pilot Study", *Forest Products Journal*, vol. 45, No. 11/12, Nov./Dec. 1995.

Ross, R.J.; McDonald, K.A.; Green, D.W.; Schad, K.C. "Stress Wave Nondestructive Evaluation of Logs to Predict Structural Product Quality" USDA Forest Service, Forest Products Laboratory, Prepared for Publication in 7th International Symposium NDE Characterization of Materials, Czech Technical University Prague, Czech Republic, Jun. 19–23, 1995.

Ross, R.J. and Pellerin, R.F. "NDE of Green Material with Stress Waves: Preliminary Results Using Dimension Lumber" *Forest Products Journal*, vol. 41, No. 6, Jun. 1991.

Ross, R.J. and Pellerin, R.F. "Nondestructuve Testing for Assessing Wood Members in Structures: A Review", Department of Agriculture, Forest Service, Forest Products Laboratory, 1991.

Sandoz, J. "Ultrasound Applications to Structural Timber" Pacific Timber Engineering Conference, Gold Coast Australia, Jul. 11–15, 1994.

Wang, Y. "Dissertation—Stress Grading of Wood Utility Poles" Department of Forest and Wood Services, Colorado State University, Fort Collins, Colorado, Fall 1987.

LOG CUTTING OPTIMIZATION SYSTEM

FIELD OF THE INVENTION

The present invention relates to wood product processing systems in general, and systems for optimizing lumber cutting decisions in particular.

BACKGROUND OF THE INVENTION

In any manufacturing business, profitability depends in part on the extent to which the conversion of raw materials into finished products is optimized. This is particularly true in the wood products industry where raw logs are cut into lumber. Currently, the decision of how to cut lumber from a log is made by having a human operator visually grade a log based on such features as the number of knots in the log, the straightness of the log, any rot, etc. Next, the log is scanned using lasers or other sensors to determine its shape and dimensions. Given the grade of a log, a price table is selected and used by the sawing system's optimizing computer to calculate the assortment of lumber sizes that maximizes the value recovered from the log. The price tables are based on lumber market values, historical sawmill recovery data and may also take into account market demand by grade and dimension.

While this method works well for sawmills selling only visually graded lumber, it does not work well for mills wanting to sell various grades of higher-valued stress-rated lumber. For instance, it is well known that for some dimensions, lumber having a high modulus of elasticity (MOE) or stiffness is worth more than lumber with a low MOE. Boards having a high MOE and appropriate strength properties can be used in such applications as floor joists or roof trusses where such properties are desired. However, the relation between stiffness and price is not always straightforward. For example, 2"×8"boards are very desirable if they meet certain stiffness and strength criteria, but not very desirable if they do not. Having an advance estimate of the structural properties of the wood allows the sawing optimization system to avoid making low stiffness/strength 2×8 lumber, and instead making either 2×6 or 2×10 lumber where the price penalties for lower structural properties are less pronounced. In the past, there has not been a practical way to predict the MOE of lumber to be produced from a log and to take the predicted MOE into consideration when making cutting decisions.

Given the shortcomings in the art, there is a need for a system that can determine and consider the potential stiffness of lumber to be cut from a log in addition to the conventional measurements of shape and dimensions in order to make a cutting decision that will maximize the profit to be made from an individual log.

SUMMARY OF THE INVENTION

The present invention is a stress wave velocity system that estimates the stiffness of lumber to be produced from a log. An accelerometer is placed against the log while the log is struck with a pneumatic hammer. Signals received from the accelerometer are analyzed to estimate the speed of a stress wave induced in a log. Once the speed of the stress wave is known, a price table is selected that relates various lumber dimensions to current market prices. A computer system within the sawmill utilizes the selected price table to maximize the value of the lumber produced from a given log.

The stress wave velocity system includes a pair of proximity sensors that determine whether a log is present. If a log is present, a sensor tube including the accelerometer and pneumatic hammer is moved on a sliding carriage to engage the log. Air stored in a pneumatic accumulator is released into the hammer such that a striking face of the hammer engages the log. Vibration signals from the accelerometer are digitized, and transformed to the frequency domain by a computer-based signal analyzer. The computer based signal analyzer searches the signal spectrum for resonance frequencies caused by the pneumatic hammer. Estimates of a length of a log are determined from a laser on one end of the log and by measuring the distance that the sensor tube is moved in order to engage the log at the other end. From the length of the log and the resonance frequency determined, the speed of the stress wave in the log can be estimated. From the speed of the stress wave, an appropriate price table is selected and used by the computer system to determine the optimum manner in which to cut lumber from the log.

BRIEF DESCRIPTION OF THE DRAWINGS

The foregoing aspects and many of the attendant advantages of this invention will become more readily appreciated as the same becomes better understood by reference to the following detailed description, when taken in conjunction with the accompanying drawings, wherein.

DETAILED DESCRIPTION OF THE PREFERRED EMBODIMENT

The present invention is a system for predicting the modulus of elasticity (MOE) or stiffness and associated structural properties of lumber to be cut from a log. By knowing the MOE of the wood in the log, more optimal decisions can be made regarding how a log is to be processed.

Figure 1:
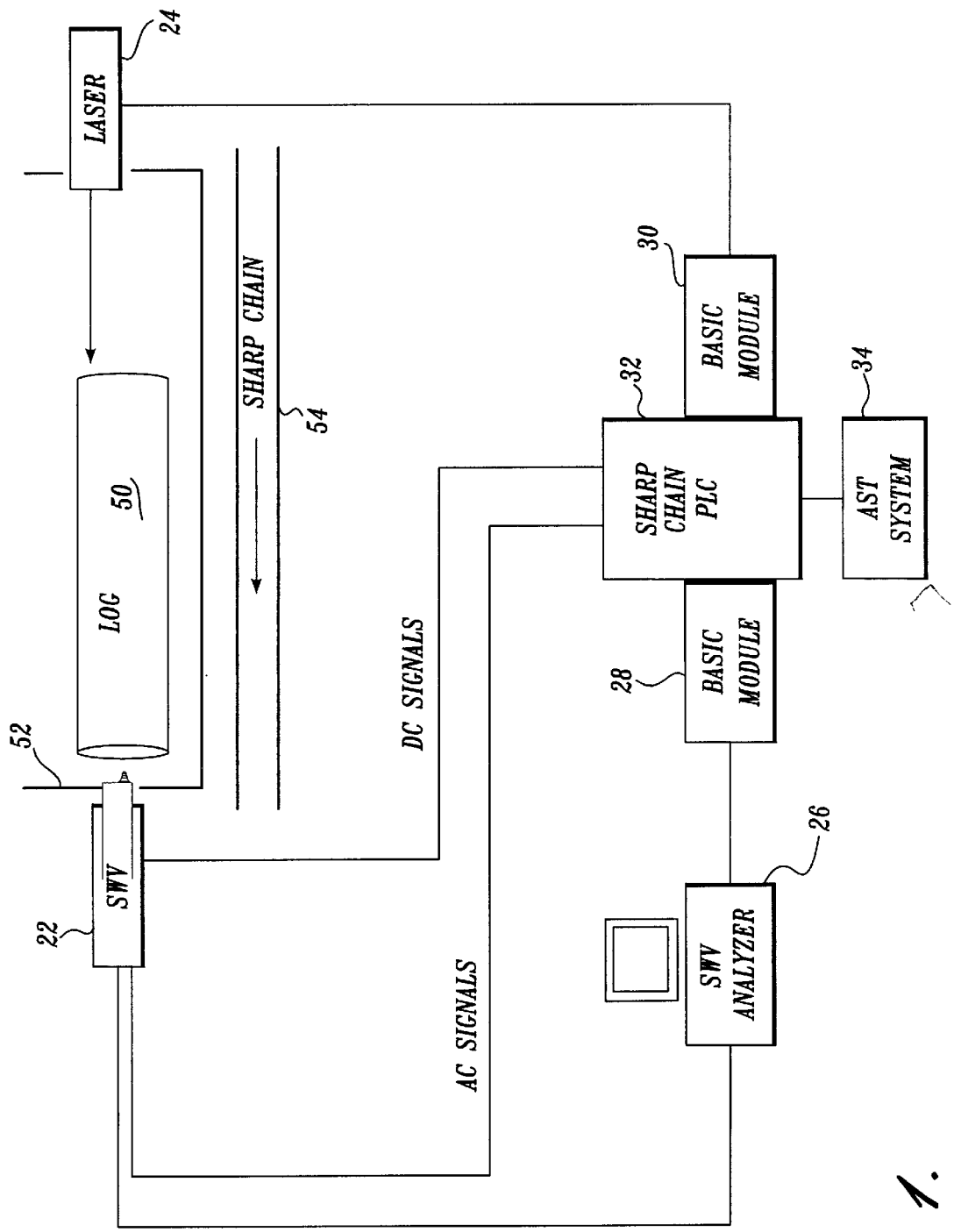
FIG. 1 is a block diagram of a stress wave velocity (SWV) system that obtains SWV's which are used to determine how logs are to be cut into lumber according to the present invention.

FIG. 1 is a block diagram of a portion of a sawmill where raw logs are received and cut into lumber. A number of logs 50 are moved towards a series of cutting saws (not shown) by a log ladder 52. At the top of the log ladder, the movement of a log is suspended for approximately two seconds while an operator of the log ladder visually grades the log. The log is then rolled onto a "sharp chain" 54 (i.e., a primary breakdown infeed system) that carries the log to the cutting saws.

To supplement the information used to make cutting decisions, the present invention is a stress wave velocity (SWV) system that determines the speed of a stress wave that is induced in a log. The SWV system includes a stress wave signal acquisition unit (SAU) 22 that engages the log 50 while it is halted on the log ladder and imparts a stress wave into the log. The distance that the SAU 22 is moved to engage the log is measured. In addition, a laser 24 is used to measure the distance to another end of the log. From these measurements, the length of the log is determined.

As will be described in further detail below, the SAU 22 strikes the log with a pneumatic hammer and picks up vibrational signals from a standing stress wave in the log with an accelerometer. From the round-trip time of the stress wave, the speed of the stress wave in the log can be estimated and correlated to a predicted MOE of the lumber to be produced from the log.

The SWV system further includes a SWV analyzing computer system 26 that receives the electronic signals produced by the accelerometer within the SAU 22. Finally, the SWV system includes a pair of basic modules 28 and 30 that provide data from the SWV analyzing computer system 26 and the laser 24 to a programmable logic controller 32. The programmable logic controller 32 controls the operation of the log ladder 52, the sharp chain 54 and the cutting saws (not shown). The controller 32 is interfaced with a computer system 34 that is part of the primary breakdown system of the sawmill that receives data from a plurality of conventional sensors (not shown) that determine the dimensions of the log including its length, diameter and taper. From these measurements, the computer system 34 determines the lumber that should be cut from the log.

To determine the speed of a stress wave in the log 50, the programmable logic controller 32 directs the SAU 22 to move toward the log 50. The distance that the SAU has to extend in order to engage the log is recorded. The distance together with the measurements made by the laser 24, allows the programmable logic controller 32 to compute the length of the log. Once the SAU has engaged the log, the programmable logic controller 32 causes the SAU 22 to impart a stress wave in the log. The vibrations caused by the stress wave are detected by the SAU and provided to the SWV analyzing computer system 26.

Because the SAU 22 is subject to a great deal of vibration that is produced from the machinery and logs moving within the sawmill, the SWV analyzing computer system 26 analyzes the signals received from the accelerometer within the SAU 22 in order to separate those signals caused by the stress wave from those induced by the background noise. To accomplish this, the SWV analyzing computer system 26 digitizes the signals received from the accelerometer. The signals are then transformed into the frequency domain using a conventional Fast Fourier Transform. Next, the SWV analyzing computer system 26 searches for resonance frequencies in the spectrum between a lowest and a maximum expected frequency.

The speed of the stress wave induced by the SAU 22 can be measured by determining the time it takes the stress wave to travel to the end of the log and back according to the equation $$S = 2L/\tau \tag{1}$$

where S is the speed of the stress wave, L is the length of the log and τ is the round trip time. In the frequency domain, the time for the stress wave to travel to the end of the log and back is related to the resonance frequency of the stress wave according the equation $$\tau = 1/f \tag{2}$$

where f is the resonance frequency of the stress wave. Therefore the speed of the stress wave, S, can be determined according to the equation $$S = 2Lf \tag{3}$$

In practice, it is known that the speed of the stress wave varies between an expected minimum of approximately 6000 feet per second to a maximum of approximately 20,000 feet per second. Therefore the spectrum of the signals produced by the accelerometer is searched for resonance frequencies that occur between a lowest expected frequency (LEF) and a maximum expected frequency (MEF) that are defined by the equations:

$$LEF = S_{min}/2L \tag{4}$$

$$MEF = S_{max}/2L \tag{5}$$

Once the resonant frequency is found, it is used in Equation 3 to compute the speed of the stress wave induced in the log by the pneumatic hammer.

From the speed of the stress wave in the log, an estimate of the modulus of elasticity or MOE of the log can be made. According to the chart set forth in Appendix A, it has been determined that the speed of the stress wave in the log varies directly with the MOE of the wood in the log. This data was obtained for Loblolly pine. As will be appreciated by those skilled in the art, the particular relationship between the speed of the stress wave and the MOE of the wood in a log may vary depending on the type of wood being analyzed, the age of the log or other factors. The particular relationship for other types of wood is determined by measuring the SWV in a log, cutting lumber from the log and following the lumber through the manufacturing process. The MOE of the lumber is then carefully measured in a laboratory and related to the SWV measured.

Once speed of the stress wave in the log has been determined, a price table for the log is selected. Appendix B illustrates the currently preferred method of selecting price tables. Stress wave velocities below 11,000 feet per second are considered to correlate to relatively low MOE'S, while stress wave velocities above 12,000 feet per second correlate to a high MOE.

As in the past, the operator of the log ladder indicates whether the log is either grade I, II or III. In addition, the operator of the log ladder indicates whether the log is from the base of a tree (the first log position) or from higher up (the second log position). This information is used to select the preferred price table. For example, a grade I log from a first position having a stress wave velocity between 11,000 and 12,000 feet per second uses price table 4. A similar log having a stress wave velocity that is greater than 12,000 feet per second uses price table 5 etc. Because the higher stress wave velocity is indicative of wood having a higher MOE, price table 5 can be constructed to reflect the premium that can be charged for the stiffer boards produced.

Once the appropriate price table is selected, the computer system 34 of the primary breakdown system uses the selected price table as well as the measurements of the log's dimensions to determine the most optimum series of cuts to make to maximize the value of the lumber produced.

Figure 2:
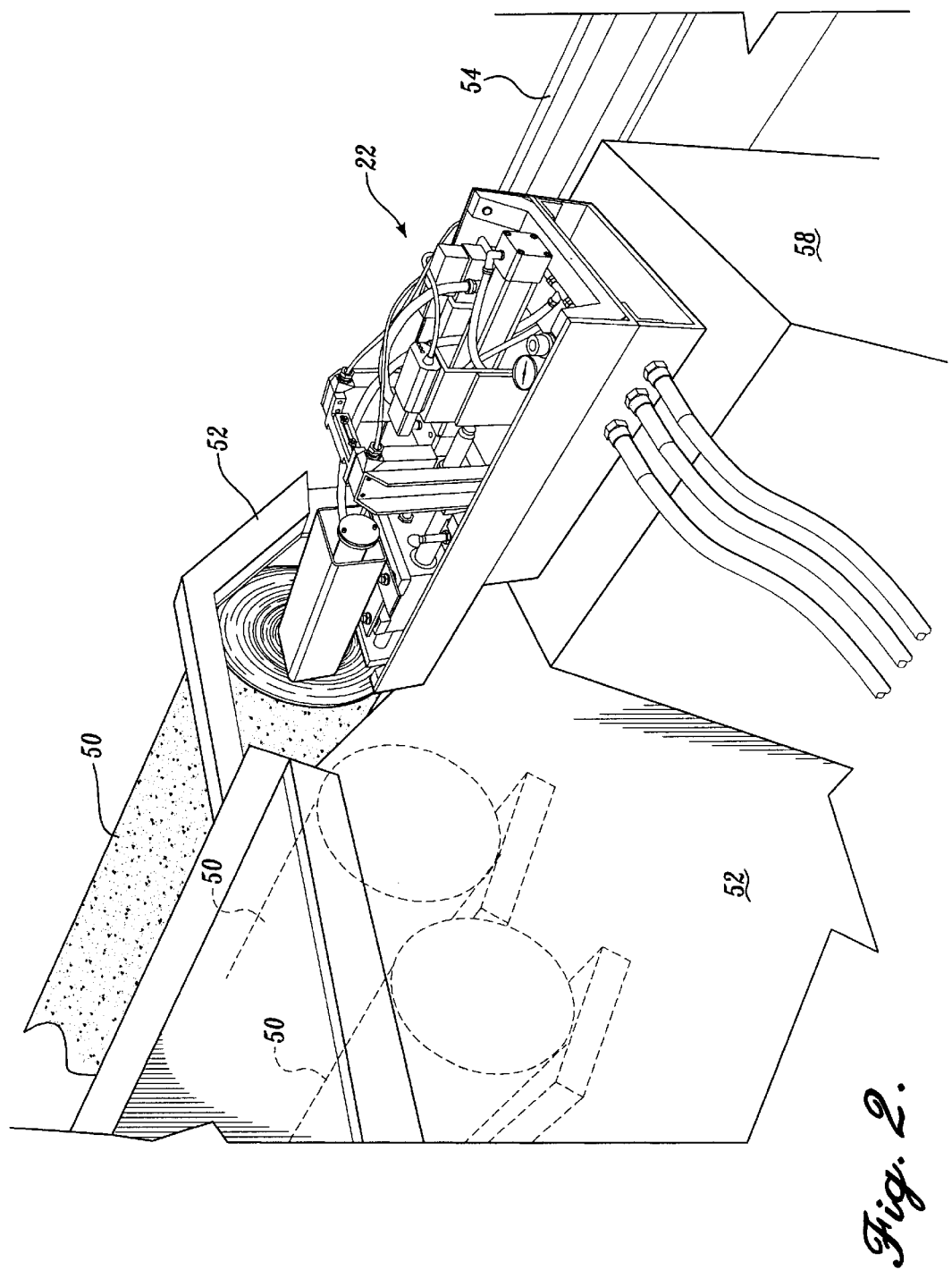
FIG. 2 is an environmental view of a stress wave signal acquisition unit (SAU) that obtains stress wave signals from a log according to the present invention.

FIG. 2 illustrates the SAU 22 in greater detail. In order to shield the stress wave SAU 22 from as much vibration as possible, the SAU is mounted on a pedestal 58 that is not coupled to the log ladder 52. The SAU 22 preferably obtains its signals from a log at the position on the log ladder where the log is halted momentarily in order to grade the log prior to being placed on the sharp chain 54. Although the SAU 22 could be located at other positions along the log ladder 52, obtaining the stress wave velocity just before the logs are placed on the sharp chain is preferable because logs will sometimes get out of order as they travel on the log ladder. If this happens, it can be difficult to associate the SWV data received with a particular log to be cut. The SAU 22 illustrated in FIG. 2 is shown without a protective cover. However, in practice a metal cover having an open end for a pneumatic hammer and an accelerometer is placed over the device to protect the components therein and to reduce the amount of dirt that enters the device.

Figure 3:
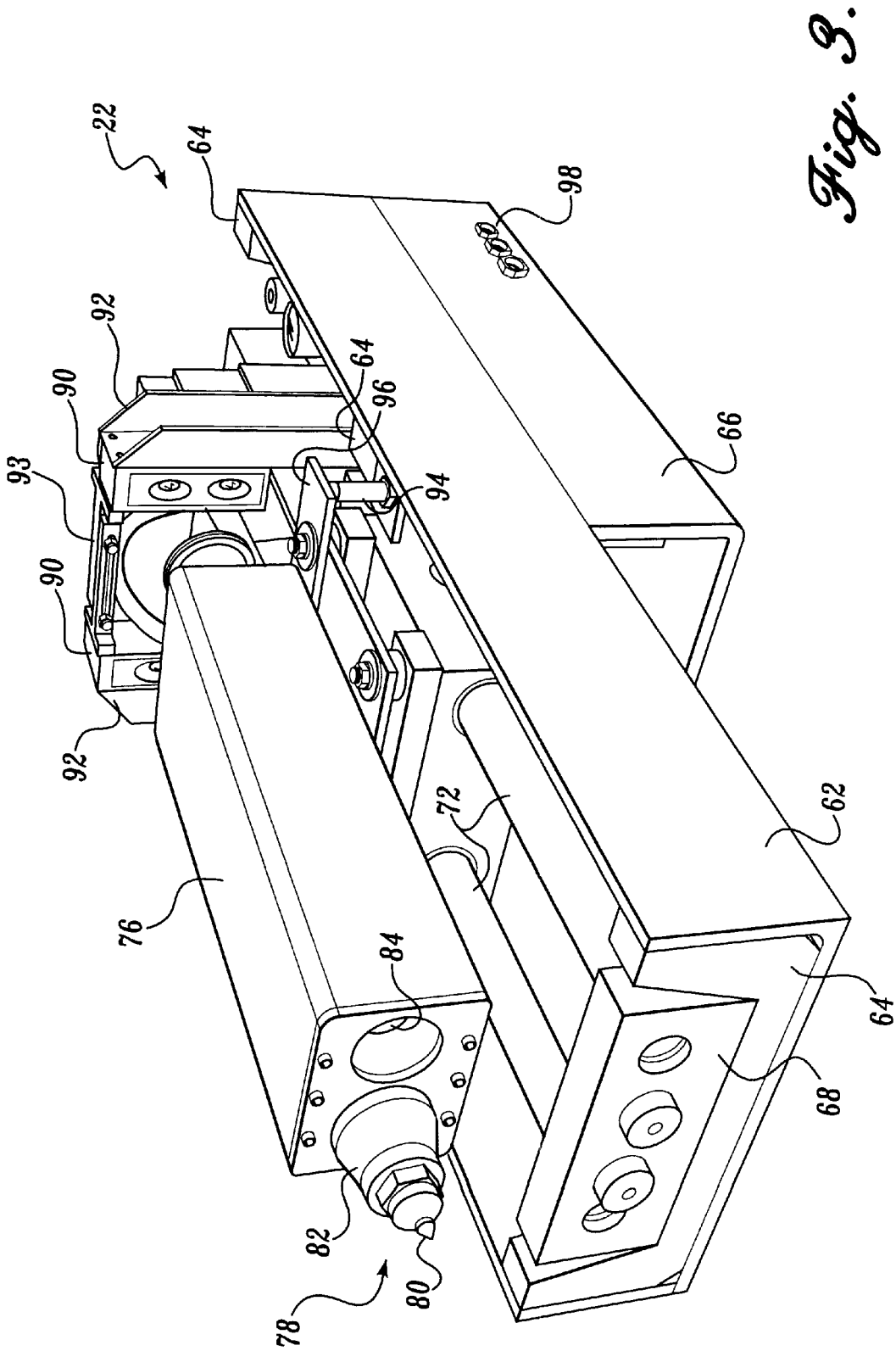
FIG. 3 is a front isometric view of the SAU according to the present invention.

As shown in FIG. 3 the SAU 22 is built on a U-shaped aluminum base channel 62 having a substantially flat bottom surface and short side walls. Disposed at equal distances along the length of the base channel are three U-shaped stiffening members 64. The stiffening members 64 have a flat base portion that is seated on the bottom surface of the base channel and a pair of arms that engage an inner surface of the side walls such that the side walls are strengthened.

To increase the height of the SAU 22, the base channel 62 is secured to a foot channel 66 that is a piece of U-shaped aluminum having the same width as the base channel. The length of the foot channel 66 is shorter than the length of the base channel 62 such that when the base channel 62 and the foot channel 66 are aligned at one end, the base channel overhangs a portion of the foot channel.

Secured to the flat portion of the stiffening members 64 is a sliding carriage 68. The sliding carriage includes a base plate 70 that is moved by a pneumatic piston back and forth along a pair of rods 72. The sliding carriage 68 is preferably equipped with rod wipers and pressurized bushings to reduce the amount of saw dust and grit that gets between the base plate 70 and the rods 72. The sliding carriage used in the presently preferred embodiment of the invention is a PHD Slide Model #SGD15x 8 available from PHD, Inc. of Fort Wayne, Ind.

Mounted to the base plate 70 of the sliding carriage 68 is a sensor tube 76. The sensor tube 76 houses an accelerometer 78 and a pneumatic hammer 84. The accelerometer 78 has a metal tip 80 that engages a cut surface on a log in order to measure vibrations caused by a stress wave within the log. The accelerometer is mounted to the sensor tube 76 with a rubber gasket 82 that shields the accelerometer from vibrations caused by the SAU 22 as well as from some of the vibrations occurring in the sawmill.

Positioned behind and on either side of the sensor tube 76 are a pair of photoelectric proximity sensors 90 that determine when a log is present in front of the SAU 22. The sensors 90 are supported by a pair of vertically extending arms 92 having one end secured to the bottom surface of the base channel 62. The arms are connected with a linkage 93 so as to form an arch behind the sensor tube 76.

When the presence of a log is detected by the photoelectric sensors 90, the sensor tube 76 on the base plate 70 is moved until the metal tip 80 of the accelerometer 78 engages the cut surface of the log. The pneumatic hammer 84 is then fired in order to impart a stress wave into the log. The accelerometer measures the longitudinal vibrations of the log in order to estimate the speed of the stress wave, which is related to the MOE or the stiffness of the wood in the log.

Also included in the base channel 62 is an inductive proximity sensor 94 that detects the presence of a metal plate 96 that extends outwardly from the base 70 of the sliding carriage 68. The proximity sensor is used to tell when the sensor tube 76 is in the fully retracted position and therefore when the log ladder can be restarted.

Finally, the foot channel 66 includes a number of pneumatic hose connectors 98 to which pneumatic hoses are inserted in order to supply the unit SAU 22 with compressed air to drive the sliding carriage 68 and fire the pneumatic hammer 84.

Figure 4:
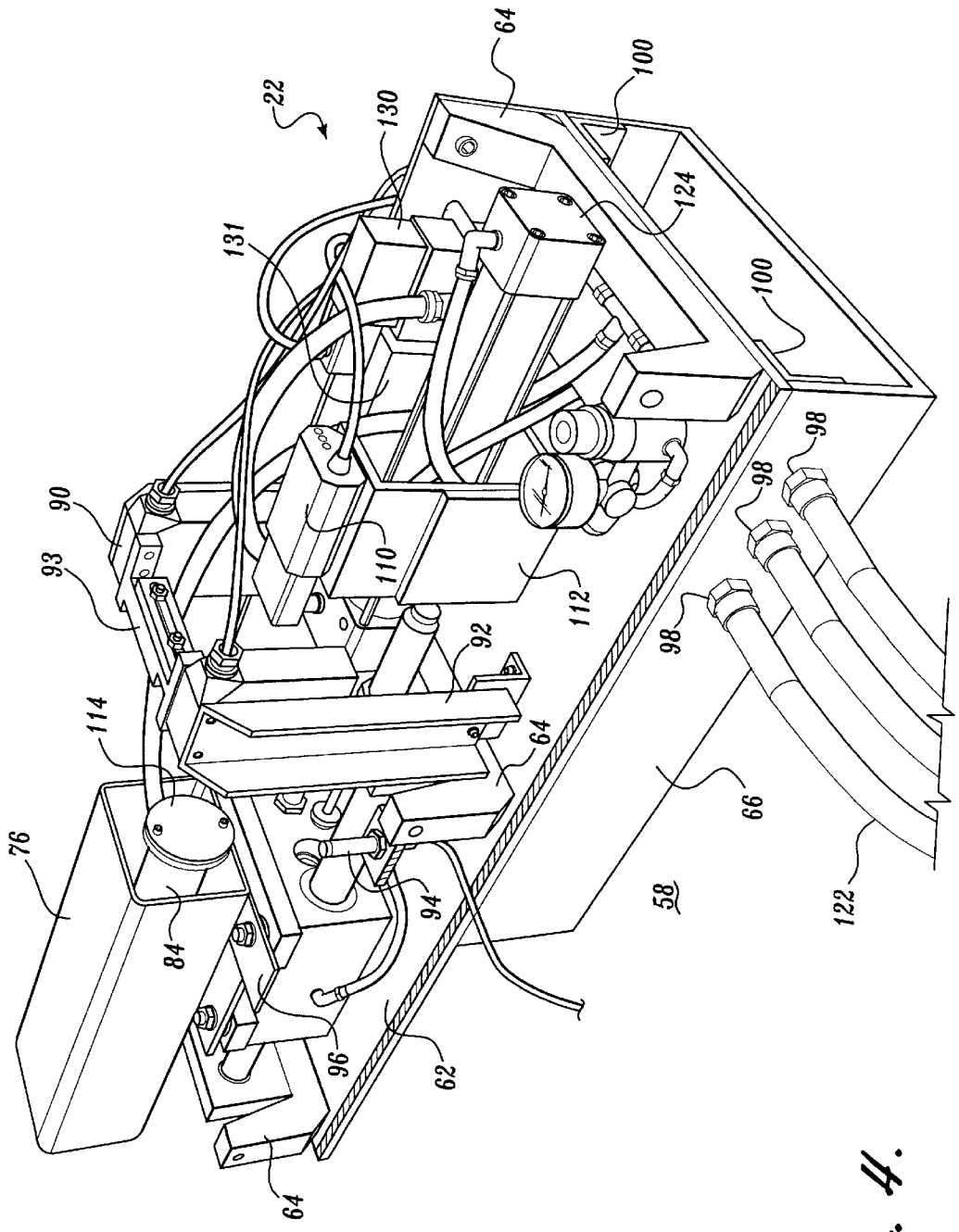
FIG. 4 is a rear isometric view of the SAU according to the present invention.

FIG. 4 shows the SAU 22 with one of the side walls of the base channel 62 removed to further illustrate the components contained therein. The foot channel 66 is secured to a bottom surface of the base channel 62 with a pair of angle brackets 100. Disposed behind the photoelectric proximity sensors 90 is another photoelectric distance sensor 110. The distance sensor 110 is mounted on a generally L-shaped bracket 112 that is secured to the bottom of the base channel 62. Light from the distance sensor 110 shines through the arch created by the arms 92 and linkage 93 that support the proximity sensors 90. The light measures the distance to a white reflecting plate 114 that is mounted to an end of the pneumatic hammer 84.

A pressure regulator 120 receives compressed air from a pneumatic hose 122 that is connected to a hose connector 98. The pressure regulator 120 provides compressed air to the pressurized bushings of the sliding carriage.

Figure 5:
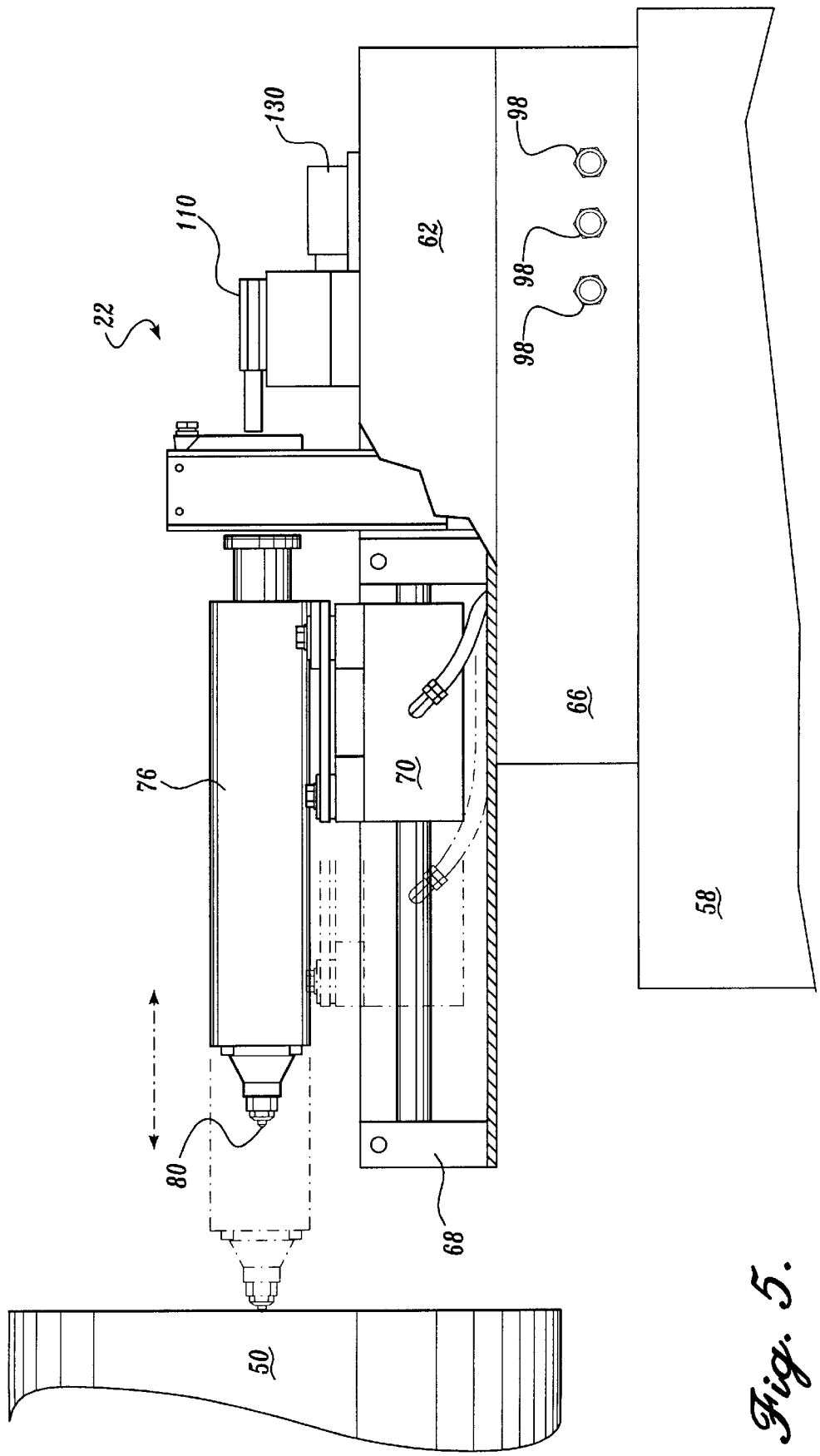
FIG. 5 is a side elevation view illustrating how the SAU engages a log.

FIG. 5 illustrates how the sensor tube 76 is extended on the base 70 of the slidable carriage 68 in order for the accelerometer to engage a cut surface at an end of a log 50. When the log 50 reaches the top of the log ladder, the base 70 of the sliding carriage is extended until the metal tip 80 of the accelerometer contacts the log. The metal tip 80 continues to be forced against the log until the pneumatic hammer is fired and the signals produced by the accelerometer have been recorded. After the signals from the accelerometer have been recorded by the SWV analyzing computer system 26 (FIG. 1), the base 70 and sensor tube 76 are retracted until the next log is ready to be measured.

Figure 6:
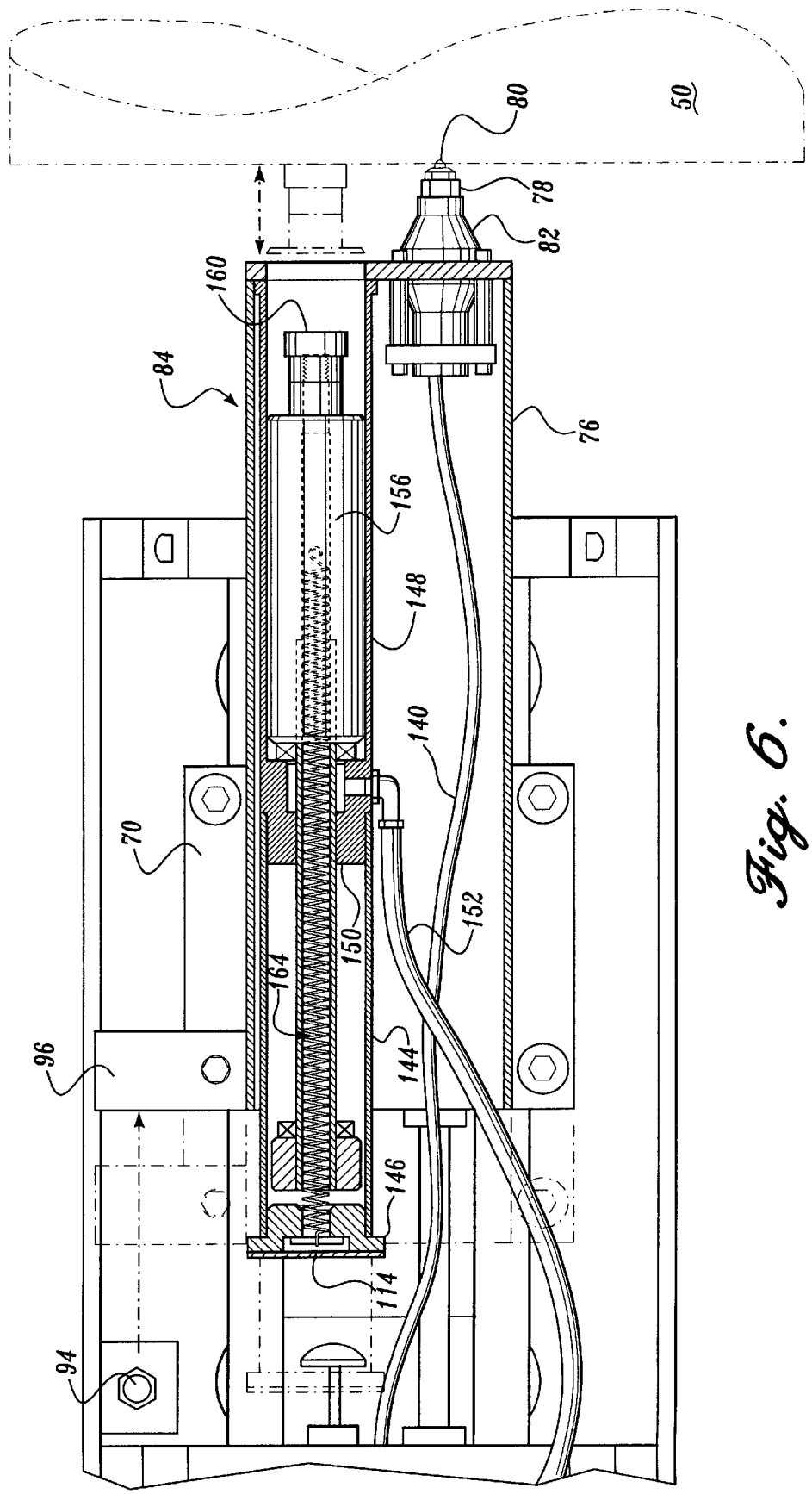
FIG. 6 is a plan view showing in detail how an accelerometer and pneumatic hammer of the SAU engage a log.

The details of the sensor tube 76 and pneumatic hammer 84 are shown in FIG. 6. As discussed above, the accelerometer 78 is mounted to a front face of the sensor tube 76 with a rubber gasket 82. The accelerometer 78 is preferably a PCB Model #328F11 available from PCB Piezotronics, Inc. of Depew, N.Y. However other accelerometers could be used. Signals from the accelerometer are carried on a cable 140 to the remotely located SWV analyzing computer system where the signals are analyzed in order to compute the speed of stress wave in the log.

The pneumatic hammer 84 comprises a cylindrical tube 144 having a cap 146 disposed at an end thereof. The reflective plate 114 is secured to the outer face of the cap 146. At the other end of the cylindrical tube 144 is a second cylindrical tube 148. The cylindrical tube 148 includes a butt section 150 that is undercut to fit within the tube 144 and form a friction fit. The butt section 150 is sealed at one end and receives compressed air from a pneumatic hose 152 that is connected to the pneumatic accumulator 131 (shown in FIG. 4). Within the second cylindrical tube 148 is a movable cylinder 156 having a hammer striking surface 160 at its distal end. When air stored in the pneumatic accumulator 131 is released by a solenoid valve 130 (FIG. 4), the air is carried by the hose 152 to the butt section 150 of the hammer. The air is then expelled from an open end of the cylindrical tube 148 thereby carrying the movable cylinder 156 forward to strike the cut surface of the log. After striking the log, the movable cylinder 156 is retrieved within the cylindrical tube 148 by a spring 164 that has one end fixed to the cap 146 at the end of the hammer.

As can be seen, the present invention provides additional information concerning how logs can be cut to maximize their economic value. By determining the velocity of a stress wave in the log, estimations can be made of the stiffness of the lumber that will be produced. This stiffness value can be factored into the determination of how the log will be cut in order to produce maximum value. Because an estimation of the MOE of the wood can be determined before the log is cut, a better use of the wood in the log can be made.

While the preferred embodiment of the invention has been illustrated and described, it will be appreciated that various changes can be made therein without departing from the spirit and scope of the invention. For example, the present invention can be used on a stem merchandiser to aid in deciding which logs should be used to make lumber or other products such as plywood etc. Stems with high SWV's could be cut into sawmill logs to produce high stiffness/strength lumber once it is determined that a stem has a high enough SWV to produce lumber, the stem can be cut into lengths that will optimize the value of the lumber produced. Stems with lower SWV's could be cut into logs for plywood where high stiffness and strength properties are not required.

The embodiments of the invention in which an exclusive property or privilege is claimed are defined as follows:

1. A method of predicting one or more structural properties of lumber to be cut from a log and to use the one or more predicted structural properties in determining how the log can be cut by a breakdown system, comprising:

measuring a length of the log;

generating a stress wave in the log;

determining a stress wave velocity in the log, the stress wave velocity being related to a modulus of elasticity of the lumber to be cut from the log;

selecting a lumber price table that is associated with the determined stress wave velocity, the price table relating lumber dimensions having a predicted modulus of elasticity to a current market value; and providing the selected price table to the lumber breakdown system that determines a set of dimensions of the log and computes how the log should be cut to maximize the value of the lumber recovered from the log.

2. The method of claim 1, wherein the step of generating a stress wave in the log comprises striking the log with a hammer.

3. The method of claim 1, wherein the step of determining the stress wave velocity further comprises the steps of:

monitoring vibrations from the log with a transducer;

receiving a signal from the transducer that is produced by the stress wave;

searching the signal from the transducer in the time domain for successive amplitude peaks representing a reflection of the stress wave generated in the log;

determining an elapsed time between the successive peaks; and from the elapsed time and the length of the log, determining the stress wave velocity.

4. The method of claim 1, wherein the step of determining the stress wave velocity further comprises the steps of:

monitoring vibrations from the log with a transducer;

receiving a signal from the transducer that is produced by the stress wave;

converting the signals received from the transducer into a frequency spectrum;

searching the frequency spectrum for resonant frequencies caused by the stress wave generated in the log; and from the resonant frequencies and the length of the log, determining the stress wave velocity.

5. The method of claim 4, wherein the step of searching the frequency spectrum for the resonant frequencies comprises the step of searching the spectrum between a minimum and a maximum expected frequency that are related to expected minimum and maximum stress wave velocities for the length of the log.

6. A system for predicting a modulus of elasticity of lumber to be cut from a log and to use the predicted modulus of elasticity in determining how the log can be cut by and optimized by a log breakdown system, comprising:

a measurement system that determines a length of the log;

a hammer that selectively strikes the log to impart a stress wave in the log;

a sensor that measures vibrations in the log from the stress wave;

a computer system that receives signals from the sensor and determines a velocity of the stress wave that is related to the modulus of elasticity of the lumber to be cut from the log, the computer system selecting a lumber price table that is associated with a predicted modulus of elasticity, wherein the lumber price table relates lumber dimensions having the predicted modulus of elasticity to a current market value, the computer system further providing the selected lumber price table to the lumber breakdown system to determine how the log should be cut to maximize the value of the lumber recovered from the log.

7. The system of claim 6, wherein computer system converts the signals received from the sensor into a frequency spectrum and searches the frequency spectrum for the resonant frequencies caused by the stress wave induced in the log.

8. The system of claim 6, wherein the sensor is an accelerometer.

9. The system of claim 8, wherein the accelerometer is mounted in a sensor tube and wherein the accelerometer is mounted to the sensor tube with a isolation gasket to shield the accelerometer from extraneous vibrations.

10. A method of processing tree stems on a merchandiser in a sawmill comprising:

measuring a length of tree stem;

generating a stress wave in the tree stem;

determining a stress wave velocity in the tree stem, the stress wave velocity being related to a modulus of elasticity of the tree stem;

selecting a price table associated with a predicted modulus of elasticity; the price table relating wood products having the predicted modulus of elasticity to a current market value; and processing the tree stem such that a value of the wood products produced from the tree stem is maximized.

* * * * *

UNITED STATES PATENT AND TRADEMARK OFFICE
CERTIFICATE OF CORRECTION

PATENT NO. : 6,026,689
DATED : February 22, 2000
INVENTOR(S) : William D. Snyder et al.

It is certified that error appears in the above-identified patent and that said Letters Patent is hereby corrected as shown below:

Claim 1,
Line 26, please delete [a] and substitute therefor -- the --.

Signed and Sealed this

Eighth Day of January, 2002

JAMES E. ROGAN
*Director of the United States Patent and Trademark Office*

*Attest:*

*Attesting Officer*